United States Patent
Aono et al.

(10) Patent No.: US 12,018,230 B2
(45) Date of Patent: *Jun. 25, 2024

(54) SURFACTANT COMPOSITION

(71) Applicant: KAO CORPORATION, Tokyo (JP)

(72) Inventors: Keita Aono, Wakayama (JP); Satoru Okamura, Wakayama (JP)

(73) Assignee: KAO CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/910,058

(22) PCT Filed: Mar. 16, 2021

(86) PCT No.: PCT/JP2021/010640
§ 371 (c)(1),
(2) Date: Sep. 8, 2022

(87) PCT Pub. No.: WO2021/187488
PCT Pub. Date: Sep. 23, 2021

(65) Prior Publication Data
US 2023/0121566 A1 Apr. 20, 2023

(30) Foreign Application Priority Data
Mar. 17, 2020 (JP) ................ 2020-046793

(51) Int. Cl.
C11D 1/831 (2006.01)
A61K 8/04 (2006.01)
A61K 8/34 (2006.01)
A61K 8/39 (2006.01)
A61K 8/46 (2006.01)
A61K 8/60 (2006.01)
A61Q 19/10 (2006.01)
C09K 23/10 (2022.01)
C11D 3/00 (2006.01)
C11D 3/20 (2006.01)
C11D 3/43 (2006.01)
C11D 17/00 (2006.01)
C11D 1/12 (2006.01)
C11D 1/29 (2006.01)
C11D 1/66 (2006.01)
C11D 1/72 (2006.01)

(52) U.S. Cl.
CPC .............. C11D 1/831 (2013.01); A61K 8/046 (2013.01); A61K 8/345 (2013.01); A61K 8/39 (2013.01); A61K 8/463 (2013.01); A61K 8/466 (2013.01); A61K 8/602 (2013.01); A61Q 19/10 (2013.01); C09K 23/10 (2022.01); C11D 3/0094 (2013.01); C11D 3/2068 (2013.01); C11D 3/43 (2013.01); C11D 17/0043 (2013.01); C11D 1/123 (2013.01); C11D 1/29 (2013.01); C11D 1/662 (2013.01); C11D 1/72 (2013.01)

(58) Field of Classification Search
CPC ........... C11D 3/43; C11D 1/83; C11D 3/2068; C11D 1/831; C11D 3/0026; C11D 3/0094; C11D 1/29; C11D 1/662; C11D 1/92; C11D 1/123; C11D 1/75; C11D 17/0043; C11D 1/94; C11D 1/02; C11D 1/72; C09K 23/017; C09K 23/10; C09K 23/16; C09K 23/04; C09K 23/56; A61Q 19/10; A61K 8/345; A61K 8/046; A61K 8/463; A61K 8/602; A61K 8/466; A61K 8/39

See application file for complete search history.

(56) References Cited

U.S. PATENT DOCUMENTS

| | | | |
|---|---|---|---|
| 2,028,091 | A | 1/1936 | Jaeger |
| 4,434,091 | A | 2/1984 | Cox et al. |
| 4,839,098 | A | 6/1989 | Wisotzki et al. |
| 5,908,582 | A | 6/1999 | Feustel et al. |
| 2007/0214999 | A1 | 9/2007 | Meyer et al. |
| 2012/0012130 | A1 | 1/2012 | Hutton, III et al. |
| 2018/0051201 | A1 | 2/2018 | Vanzin et al. |
| 2018/0201885 | A1 | 7/2018 | Bittner et al. |

FOREIGN PATENT DOCUMENTS

| | | |
|---|---|---|
| JP | S58-24555 A | 2/1983 |
| JP | S63-225697 A | 9/1988 |
| JP | H09-500884 A | 1/1997 |
| JP | 2008260852 A | 10/2008 |
| JP | 2012172032 A * | 9/2012 |
| JP | 2013100462 A | 5/2013 |
| JP | 2013532736 A | 8/2013 |
| JP | 2017214554 A | 12/2017 |
| JP | 2018529989 A | 10/2018 |
| JP | 2019104852 A | 6/2019 |
| WO | WO-2013054635 A1 | 4/2013 |
| WO | WO-2017204149 A1 | 11/2017 |

OTHER PUBLICATIONS

English translation of the International Preliminary Report on Patentability and Written Opinion mailed Sep. 29, 2022 in PCT/JP2021/010640, 6 pages.

International Search Report issued Jun. 15, 2021 in PCT/JP2021/010640 (with English translation), 7 pages.

* cited by examiner

Primary Examiner — Vishal V Vasisth
(74) Attorney, Agent, or Firm — Element IP, PLC

(57) ABSTRACT

The present invention is a surfactant composition containing (a) a branched alkyl sulfosuccinate ester having a branched alkyl group with 9 or 10 carbons and (b) a surfactant [excluding (a)].

10 Claims, No Drawings

SURFACTANT COMPOSITION

This application is a 371 of PCT/JP2021/010640 filed Mar. 16, 2021.

FIELD OF THE INVENTION

The present invention relates to a surfactant composition, a foaming control agent and a foaming control method.

BACKGROUND OF THE INVENTION

Compositions containing surfactants are applied in clothing detergents, skin cleaning agents, household cleaning agents, tableware detergents or the like. Further, not only the ability to clean the target dirt but also the control of foaming performance such as foamability, foam persistence or the like are required of these compositions depending on their uses or purposes. For example, technologies of using a combination of foaming surfactants or technologies of using foam enhancing agents together are commonly used for such control of foaming performance.

JP-A 2013-100462 discloses a technology of a detergent composition for hand-washing of tableware comprising di-2-ethylhexyl sulfosuccinate, wherein the composition exhibits rich foaming during washing and foam persistence during washing, but foam disappears instantaneously during rinsing, so that rinsing is completed with a small amount of water.

JP-A 2013-532736 discloses a surfactant with a branched structure excellent in lathering and lathering stability.

JP-A 2017-214554 discloses a tableware detergent composition comprising a predetermined alkyl sulfosuccinate ester with a hyperbranched structure.

JP-A 2018-529989 discloses use of a composition comprising an ammonium salt of a specific compound such as a sulfobutanedioic acid diester or the like, for cleaning or rinsing a product comprising a substrate and a patterned material layer supported thereon, the patterned material layer having line-space structures with a line width of 50 nm and below.

US-A 2007/0214999 discloses a composition comprising (a) one or more salts of a mono- and/or dialkyl ester of a sulfonated dicarboxylic acid, wherein the dicarboxylic acid contains 4 to 8 carbon atoms and the alkyl groups are derived from 2-propylheptanol, and (b) an organic solvent.

JP-A H9-500884 discloses the use of a liquid composition containing a sulfosuccinic acid diester with a predetermined structure as a wetting agent and an emulsifier.

SUMMARY OF THE INVENTION

In general, foam formed during washing is often preferred by workers because it gives them the feeling that they perform washing. Further, the foam also has the advantage that portions to be washed can be clearly identified by foam adhesion, or the like, and may sometimes also be required to have excellent foam stability.

The present invention provides a surfactant composition excellent in foamability and foam stability, and a foaming control agent and a foaming control method capable of imparting excellent foamability and foam stability to a composition containing a surfactant.

The present invention relates to a surfactant composition containing (a) a branched alkyl sulfosuccinate ester in which the branched alkyl group is a branched alkyl group with 9 or 10 carbons [hereinafter referred to as component (a)] and (b) a surfactant [excluding component (a)] [hereinafter referred to as component (b)].

Further, the present invention relates to a foaming control agent composed of (a) a branched alkyl sulfosuccinate ester in which the branched alkyl group is a branched alkyl group with 9 or 10 carbons [hereinafter referred to as component (a)] for use in a composition containing a surfactant other than component (a).

Further, the present invention relates to a method for controlling the foaming of a surfactant composition including, adding (a) a branched alkyl sulfosuccinate ester having a branched alkyl group with 9 or 10 carbons [hereinafter referred to as component (a)] to a composition containing (b) a surfactant other than component [hereinafter referred to as component (b)] to control the foaming of the composition.

According to the present invention, provided are a surfactant composition excellent in foamability and foam stability, and a foaming control agent and a foaming control method capable of imparting excellent foamability and foam stability to a composition containing a surfactant.

EMBODIMENTS OF THE INVENTION

In general, many surfactants are foamable, and making use of such a property, they are applied in detergents or the like. When a composition including a surfactant and water is mixed with gas, there is formed at the gas-liquid interface a layer of the structure that the hydrophobic part of the surfactant (an alkyl group or the like) is oriented toward the gas and the hydrophilic part toward the liquid, and water is incorporated into this layer to form foam. On the other hand, water incorporated into the layer of the surfactant is discharged over time to break the foam. From this viewpoint, it is considered that the higher the packability of the hydrophobic group is, the better the foamability is, and also, the more stable the formed foam is.

In the present invention, the combination of components (a) and (b) improves foamability and foam stability. The reason for this is not clear, but it is considered that, if the compound having an alkyl group with a specific branched structure of component (a) is present in a film of the hydrophobic part of the surfactant of component (b) in foam, the film of the hydrophobic part, which is relatively high in crystallinity, is restored by the compound of component (a), which is moderately flexible and relatively low in crystallinity, before the film of the hydrophobic part is broken to break the foam, so that foam breaking is suppressed. The effect of the present invention is unpredictable those skilled in the art as component (a), due to its structure, is considered to be a component that rather reduces the packability of the film of the hydrophobic part formed by component (b).

<Surfactant Composition>

Component (a) is a branched alkyl sulfosuccinate ester having a branched alkyl group, wherein the branched alkyl group is a branched alkyl group with 9 or 10 carbons.

Examples of component (a) include those in which the ester is a monoester and those in which the ester is a diester. Preferable is a branched alkyl sulfosuccinate diester in which the branched alkyl groups are branched alkyl groups with 9 or 10 carbons.

The branched alkyl group of component (a) is preferably a branched alkyl group having a main chain with 6 or 7 carbons and one or more side chains, the side chains having 3 carbons in total from the viewpoint of achieving both foamability and foam stability.

The branched alkyl group of component (a) is preferably a branched alkyl group selected from a 2-propylheptyl group and a 3,5,5-trimethylhexyl group.

Component (a) may be a salt. In other words, component (a) may be a compound selected from branched alkyl sulfosuccinate esters having a branched alkyl group with 9 or 10 carbons and salts thereof. Examples of the salts include inorganic salts such as sodium salts, potassium salts, ammonium salts, magnesium salts or the like, and organic salts such as monoethanolamine salts, diethanolamine salts, triethanolamine salts, morpholine salts or the like. The salts for component (a) are preferably inorganic salts selected from alkali metal salts such as sodium salts, potassium salts or the like and alkaline earth metal salts such as magnesium salts or the like, and more preferably alkali metal salts.

Examples of component (a) include a branched sulfosuccinate ester represented by the following general formula (a1):

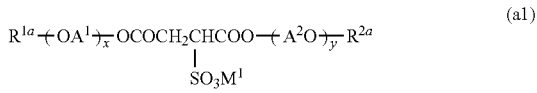

wherein $R^{1a}$ and $R^{2a}$ are each independently a branched alkyl group with 9 or 10 carbons; $A^1$ and $A^2$ are each independently an alkylene group with 2 or more and 4 or less carbons, and x and y are average numbers of added moles and each independently 0 or more and 6 or less; and $M^2$ is a hydrogen atom or a cationic ion.

The numbers carbons in $R^{1a}$ and $R^{2a}$ may be the same or different.

In the present invention, an open-chain branched hydrocarbon group includes a secondary alcohol from which a hydroxy group is removed to leave a hydrocarbon residue.

In the open-chain branched hydrocarbon group (branched alkyl group) of $R^{1a}$ or $R^{2a}$ in the present invention, the hydrocarbon chain having the largest number of carbons counted from the carbon atom bonded to the oxygen atom is considered a main chain, and a hydrocarbon chain branched from and bonded to the main chain is considered a side chain.

When there are two or more possible main chains, i.e., when there are two or more hydrocarbon chains having the largest number of carbons (hereinafter also referred to as the longest hydrocarbon chains), the main chain is determined in the following order:

1. the longest hydrocarbon chain from which a side chain having a larger number of carbon atoms is branched is considered the main chain;
2. next, when the side chains branched from the longest hydrocarbon chains have the same number of carbon atoms, the longest hydrocarbon chain from which a larger number of side chains are branched is considered the main chain;
3. next, when the same number of side chains are branched from the longest hydrocarbon chains, the longest hydrocarbon chain having a side chain at a carbon atom which is closer to the oxygen atom when counted from the carbon atom bonded to the oxygen atom is considered the main chain; and
4. next, when the carbon atoms having a side chain at the position closest to the oxygen atom are equally close to the oxygen atom, the longest hydrocarbon chain in which the side chain closest to the oxygen atom has a larger number of carbon atoms is considered the main chain.

Note that when there are two or more longest hydrocarbon chains having the same symmetric structure, any of them may be considered the main chain.

The total numbers of carbons constituting side chains in the branched alkyl groups of $R^{1a}$ and $R^{2a}$ may be the same or different and are each preferably 3 from the viewpoint of foam stability.

In the present invention, the total number of carbons constituting side chains is the total number of carbons in all the side chains other than the main chain in one branched alkyl group, and when there is a plurality of side chains, it is the total number of carbons in all those side chains.

The numbers of side chains in $R^{1a}$ and $R^{2a}$ may be the same or different, and are each 1 or more, and preferably 3 or less and more preferably 2 or less from the viewpoints of foamability and foam stability.

In the present invention, the number of side chains is the number of side chains branched from a main chain, and even if the side chains have side chains further branched from the side chains, the main chain is considered to have the same number of side chains. Note that the side chains may have side chains further branched from the side chains from the viewpoint of foamability.

The numbers of branching carbons in $R^{1a}$ and $R^{2a}$ may be the same or different, and are each 1 or more, and preferably 3 or less and furthermore preferably 2 or less from the viewpoints of foamability and foam stability.

In the present invention, the number of branching carbons is the total of the numbers of tertiary carbon atoms and quaternary carbon atoms in an open-chain branched hydrocarbon group.

In a preferable aspect for $R^{1a}$ and $R^{2a}$, the open chain branched hydrocarbon groups of $R^{1a}$ and $R^{2a}$ each independently have 9 or 10 carbons in total, each independently have a main chain with 6 or 7 carbons, each independently have a side chain with 1 or more and 3 or less constituting carbons and each independently have one side chain.

Specific branched alkyl groups of $R^{1a}$ and $R^{2a}$ may be the same or different, and are each preferably a branched alkyl group selected from a 2-propylheptyl group and a 3,5,5-trimethylhexyl group.

In the general formula (a1), $A^1$ and $A^2$ are each independently an alkylene group with 2 or more, and 4 or less and preferably 3 or less carbons.

In the general formula (a1), x and y are average numbers of added moles, and each independently 0 or more, and 6 or less, preferably 4 or less and more preferably 2 or less, and further preferably 0 from the viewpoints of foamability and foam stability.

Further, x+y is preferably 0 or more, and preferably 12 or less, more preferably 6 or less and further preferably 3 or less, and furthermore preferably 0 from the viewpoints of foamability and foam stability.

In the general formula (a1), $M^1$ is a hydrogen atom or a cationic ion. Examples of the cationic ion include inorganic cationic ions such as sodium ion, ammonium ion, potassium ion, magnesium ion or the like, and organic cationic ions such as monoethanol ammonium ion, diethanol ammonium ion, triethanol ammonium ion, morpholinium ion or the like. $M^1$ is preferably an inorganic cationic ion selected from alkali metal ions such as sodium ion, potassium ion or the like and alkaline earth metal ions such as magnesium ion or the like, and more preferably an alkali metal ion.

A method for preparing a compound in which $R^{1a}$ and $R^{2a}$ are the same in the general formula (a1) is not particularly limited, but such a compound can be produced, for example, by referring to the method described in US-B U.S. Pat. No. 2,028,091, and an asymmetric compound in which $R^{1a}$ and $R^{2a}$ are different can be produced, for example, by referring to JP-A S58-24555 for a method for preparing the same. An alcohol with a predetermined number of carbons to which an alkylene oxide is added can be used as a raw material for component (a).

Examples of suitable alcohols used to produce component (a) of the present invention include:
(1) primary alcohols represented by 3,5,5-trimethylhexane-1-ol, 2-propylheptan-1-ol or the like; and
(2) secondary alcohols represented by 5-nonanol, 2,6-dimethyl-4-heptanol or the like.

In the present invention, component (a) can be used to provide a surfactant composition excellent in foamability and foam stability.

The surfactant composition of the present invention contains component (a) in an amount of preferably 0.05 mass % or more, more preferably 0.1 mass % or more and further preferably 0.25 mass % or more, and preferably 20 mass % or less, more preferably 15 mass % or less, further preferably 10 mass % or less and furthermore preferably mass % less from the viewpoints of foamability and foam stability.

Note that, in the present invention, descriptions relating to mass pertaining to component (a) (mass % or mass ratio) are based on the mass of a compound in the form of a sodium salt, for example, the mass when $M^1$ in the general formula (a1) is assumed to be sodium.

Component (b) is a surfactant [excluding component (a)].

Examples of component (b) include one or more surfactants selected from anionic surfactants other than component (a), nonionic surfactants, cationic surfactants and amphoteric surfactants. Component (b) is preferably one or more surfactants selected from nonionic surfactants and anionic surfactants. Component (b) is preferably a surfactant rich in foaming performance.

Examples of the anionic surfactants other than component (a) can include alkyl sulfates, polyoxyalkylene alkyl ether sulfates, alkane sultanates, alkyl benzene sulfonates, higher fatty acids or salts thereof, polyoxyethylene alkyl ether carboxylic acids or salts thereof, N-acyl amino acids or salts thereof, alkyl phosphates, polyoxyethylene alkyl ether phosphates or the like. The alkyl groups in the anionic surfactants have, for example, 8 or more and 20 or less carbons. The oxyalkylene groups, for example, the oxyethylene groups, in the anionic surfactants have an average number of added moles of, for example, 0 or more and 4 or less and preferably more than 0 and 4 or less. The salts of the anionic surfactants are, for example, alkali metal salts such as sodium salts, potassium salts or the like.

The anionic surfactants other than component (a) are preferably compounds of the following general formula (b1):

$$R^{1b}-(OA^{1b})_p-OSO_3M \qquad (b1)$$

wherein $R^{1b}$ is a hydrocarbon group, preferably an alkyl group, with 10 or more and 16 or less carbons, $A^{1b}$ is an alkylene group with 2 or 3 carbons and preferably an ethylene group, and p is an average number of added moles, and 0 or more and 5 or less, preferably 0 or more and 3 or less and more preferably 0 or more and 2.5 or less; and M is a hydrogen atom or a cationic ion.

Examples of the cationic ion of M in the general formula (b1) include inorganic cationic ions such as sodium ion, ammonium ion, potassium ion, magnesium ion or the like, and organic cationic ions such as monoethanol ammonium ion, diethanol ammonium ion, triethanol ammonium ion, morpholinium ion or the like. M is preferably an inorganic cationic ion selected from alkali metal ions such as sodium ion, potassium ion or the like and alkaline earth metal ions such as magnesium ion or the like, and more preferably an alkali metal ion.

Examples of the nonionic surfactants can include alkyl monoglyceryl ethers, polyoxyalkylene monoalkyl or alkenyl ethers, alkyl ((poly)glycosides (glycoside-type nonionic surfactants), sorbitan-based nonionic surfactants, aliphatic alkanolamides, fatty acid monoglycerides, sucrose fatty acid esters, and amides of aiaanolamines such as monoethanolamine, diethanolamine, methyl monoethanolamine or the like with fatty acids such as lauric acid, myristic acid or the like. The alkyl groups or the alkenyl groups in the nonionic surfactants have, for example, 6 or more and 18 or less carbons. The oxyalkylene groups, for example, the oxyethylene groups, in the nonionic surfactants have an average number of added moles of, for example, 3 or more and 25 or less.

The nonionic surfactants are preferably one or more nonionic surfactants selected from polyoxyalkylene monoalkyl or alkenyl ethers and alkyl (poly)glycosides (glycoside-type nonionic surfactants).

The polyoxyalkylene monoalkyl or alkenyl ethers are preferably compounds of the following general formula (b2):

$$R^{2b}-O-(A^{2b}O)_n-H \qquad (b2)$$

wherein $R^{2b}$ is a hydrocarbon group, preferably an alkyl group, with 10 or more and 18 less and preferably 10 or more and 14 or less carbons, $A^{2b}$ is an alkylene group with 2 or 3 carbons and preferably an ethylene group, and n is an average number of added moles, and a number of 3 or more and 25 or less, preferably 3 or more and 20 or less and more preferably 3 or more and 15 or less.

Further, the alkyl glycosides are preferably compounds of the following general formula (b3):

$$R^{3b}-(OR^{4b})_m G_z \qquad (b3)$$

wherein $R^{3b}$ is a linear alkyl group with 8 or more and preferably 10 or more, and 16 or less and preferably 14 or less carbons; $R^{4b}$ is an alkylene group with 2 or more and 4 or less carbons, preferably an ethylene group or a propylene group and more preferably an ethylene group; G is a residue derived from a reducing sugar; m is a number of 0 or more and 6 or less on average; and z is a number of 1 or more, and 10 or less, preferably 5 or less and more preferably 2 or less on average.

Such surfactants as are represented by the general formulas (b1), (b2) and (b3) are preferable as surfactants rich in foaming performance in the present invention.

Examples of the amphoteric surfactants can include N-alkanoylaminopropyl-N,N-dimethlamine oxide, N-alkyl-N,N-dimethylamine oxide, N-alkanoylaminopropyl-N,N-dimethyl-N-carboxymethylammonium betaine, N-alkyl-N,N-dimethyl-N-caboxymethylammonium betaine, N-alkyl-N,N-dimethyl-N-sulfopropylammonium sulfobetaine, N-alkyl-N,N-dimethyl-N-(2-hydroxysulfopropyl) ammonium sulfobetaine, N-alkanoylaminopropyl-N,N-dimethyl-N-sulfopropyl ammonium sulfobetaine and N-alkanoylaminopropyl-N,N-dimethyl-N-(2-hydroxysulfopropyl) ammonium sulfobetaine. The alkanoyl groups therein are, for example, lauroyl or myristyloyl. Further, the alkyl groups therein are, for example, lauryl groups or myristyl groups.

Component (b) is preferably one or more surfactants selected from polyoxyalkylene alkyl ether sulfates, polyoxyalkylene monoalkyl or alkenyl ethers and alkyl (poly) glycosides (glycoside-type nonionic surfactants).

A mass ratio of the content component (a) to the content of component (b) in the surfactant composition of the present invention, component (a)/component (b), is preferably 0.05 or more, more preferably 0.1 or more, further preferably 0.2 or more and furthermore preferably 0.5 or more, and preferably 5 or less, more preferably 1.5 or less, more preferably 1.25 or less and further preferably 1.0 or less. In the present invention, the mass of component (a) is expressed in terms of the mass of component (a) as a sodium salt. Further, when component (b) is an anionic surfactant, the mass component (b) is expressed in terms of the mass of component (b) as a sodium salt. When component (b) is a cationic surfactant, the mass of component (b) is expressed in terms of the mass of component (b) as a chloride salt.

The surfactant composition of the present invention contains component (b) in an amount of preferably 0.1 mass % or more, more preferably 0.15 mass % or more and further preferably 0.25 mass % or more, and preferably 35 mass % or less, more preferably 20 mass % or less, further preferably 10 mass % or less and furthermore preferably mass % less from the viewpoint of foaming performance.

The surfactant composition of the present invention may contain a solvent as component (c) for the purpose of improving storage stability or adjusting viscosity. A water-soluble organic solvent with preferably 2 or more and more preferably 3 or more, and preferably 10 or less and more preferably 8 or less carbons is suitable as component (c) from the viewpoint of improving storage stability.

Preferable as component (c) are one or more water-soluble organic solvents selected from the following: (c1) monohydric or polyhydric alcohols, preferably monohydric or polyhydric alcohols selected from ethanol, isopropyl alcohol, ethylene glycol, propylene glycol, diethylene glycol, dipropylene glycol, glycerin, isoprene glycol and benzyl alcohol; and (c2) glycol ethers, preferably glycol ethers selected from propylene glycol monomethyl ether, propylene glycol monoethyl ether, 3-methyl-3-methoxybutanol, phenoxyethanol, phenyl glycol, phenoxyisopropanol, butyldiglycol (diethylene glycol monobutyl ether) and dibutylene glycol. Preferable monohydric or polyhydric alcohols are one or more selected from benzyl alcohol, ethanol and propylene glycol. Preferable glycol ethers are one or more selected from butyldiglycol and phenoxyethanol, and butyldiglycol is more preferable. Component (c) is preferably one or more water-soluble organic solvents selected from monohydric alcohols and glycol ethers. Component (c) is more preferably one or more water-soluble organic solvents selected from benzyl alcohol, ethanol, propylene glycol, butyldiglycol and phenoxyethanol. The surfactant composition of the present invention preferably contains butyldiglycol as component (c).

Here, a water-soluble organic solvent refers to a solvent with an octanol/water partition coefficient (LogPow) of 3.5 or less.

The surfactant composition of the present invention contains component (c) in an amount of preferably 1 mass % or more, more preferably 2 mass % or more and further preferably 3 mass % or more, and preferably 15 mass % or less, more preferably 12 mass % or less and further preferably 8 mass % or less from the viewpoints of storage stability and viscosity adjustment.

The surfactant composition of the present invention preferably contains water. It is preferably a liquid composition containing water.

The surfactant composition of the present invention can contain components such as, for example, hydrotrope agents or the like as optional components.

The surfactant composition of the present invention may have a pH of, for example, 2 or more, further 4 or more and further 5 or more, and 10 or less, further 9 or less, further 8 or less and further 7 or less at 25° C. The can be appropriately selected depending on uses of the surfactant composition, for example, considering irritation to hand skin or the like. The pH can be measured by a glass electrode method.

The surfactant composition of the present invention has a viscosity of, for example, preferably 3 mPa·s or more and more preferably 10 mPa·s or more, and preferably 5,000 mPa·s or less and more preferably 2,500 mPa·s or less at 25° C., though it depends on uses or the like. The viscosity can be adjusted with solvents, hydrotrope agents or the like. This viscosity can be measured by a Brookfield viscometer.

The surfactant composition of the present invention is excellent in foamability and foam stability, and thus be used for various applications by taking advantage of these properties. For example, the surfactant composition of the present invention can be suitable for use as a surfactant for detergents. Examples of the detergents include clothing detergents, skin cleaning agents, household cleaning agents, tableware detergents or the like.

The present invention provides a method for producing a surfactant composition including, mixing components (a) and (b). The matters stated in the surfactant composition of the present invention can be appropriately applied to this producing method. This producing method may be a method for producing the surfactant composition of the present invention. This producing method is a method for producing a surfactant composition including, mixing components (a) and (b), wherein it is preferable that component (b) be one or more surfactants selected from nonionic surfactants and anionic surfactants other than component (a), and components (a) and (b) be mixed such that a mass ratio a mixing amount of component (a) to a mixing amount of component (b), component (a)/component (b), is 0.05 or more, further 0.1 or more, further 0.2 or more and further 0.5 or more, and further 5 or less, further 1.5 or less, further 1.25 or less and further 1.0 or less. In this producing method, component (c) can be optionally mixed.

<Foaming Control Agent and Foaming Control Method>

The present invention relates to a foaming control agent composed of (a) a branched alkyl sulfosuccinate ester in which the branched alkyl group is a branched alkyl group with 9 or 10 carbons [hereinafter referred to as component (a)] for use in a composition containing a surfactant other than component (a).

Specific examples or preferable aspects for component (a) are the same as those in the surfactant composition of the present invention.

The matters stated in the surfactant composition of the present invention can be applied to the foaming control agent of the present invention.

The surfactant composition of the present invention may be a surfactant composition containing component (a) as a foaming control agent.

The present inventors found out that component (a) can control foaming performance of a composition containing a surfactant other than component (a) [hereinafter referred to as component (b)]. Here, the control of foaming performance typically refers to, for example, enhancing foamability and further stabilizing foam.

In general, many surfactants exhibit foamability and exhibit foamability especially when they are used together with water. Component (a) can control foaming performance of surfactants, for example, foaming performance of surfactants when they are used together with water. Component (a) can improve, for example, foamability and foam stability of the composition containing the surfactant of component (b). Component (a) may be a modifying agent used in a composition exhibiting foamability for example, a foaming composition containing component (b). In other words, component (a) may be a modifying agent for use in foaming compositions. Note that specific examples or preferable aspects for component (b) are also the same as those in the surfactant composition of the present invention.

The foaming control agent of the present invention or the above modifying agent is used such that a mass ratio of component (a) to component (b), component (a)/component (b), is preferably 0.01 or more, more preferably 0.05 or more and further preferably 0.1 or more, and preferably 1.5 or less, more preferably 1 or less and further preferably 0.5 or less.

The present invention provides a method for controlling foaming performance of a composition containing component (b) by component (a). In other words, the present invention provides a method for controlling foaming performance of a surfactant composition including, adding component (a) to a composition containing component (b) to control foaming performance of the composition. Examples of the control method of the present invention include, for example, a method for controlling foaming performance of a composition containing component (wherein component (a) is added to the composition such that a mass ratio of component (a) to component (b), component (a)/component (b), is preferably 0.01 or more, more preferably 0.05 or more and further preferably 0.1 or more, and preferably 1.5 or less, more preferably 1 or less and further preferably 0.5 or less. Component (b) is preferably one or more surfactants selected from nonionic surfactants and anionic surfactants other than component (a). The control of foaming performance may include at least one of the improvement of foamability and stabilization of foam. The present invention also provides a method of using component (a) to control foaming performance of a composition containing component (b). In these methods, specific examples or preferable aspects for component (a) are also the same as those in the surfactant composition of the present invention. Further, the matters stated in the surfactant composition of the present invention can be applied to these methods. The above composition can optionally contain component (c).

<Aspects of the Present Invention>

The following aspects of the present invention are described by way of example. The matters stated in the surfactant composition, the foaming control agent and the method for controlling foaming performance of a surfactant composition of the present invention can be appropriately applied to these aspects.

<1>
A surfactant composition containing (a) a branched alkyl sulfosuccinate ester having a branched alkyl group with 9 or 10 carbons [hereinafter referred to as component (a)] and (b) a surfactant [excluding component (a)] [hereinafter referred to as component (b)].

<2>
The surfactant composition according to <1>, wherein the branched alkyl group of component (a) is a branched alkyl group having a main chain with 6 or 7 carbons and one or more side chains the side chains having 3 carbons in total.

<3>
The surfactant composition according to 1> or <2>, wherein the branched alkyl group of component (a) is a branched alkyl group selected from a 2-propylheptyl group and a 3,5,5-trimethylhexyl group.

<4>
The surfactant composition according to any of <1> to <3>, wherein component (is a branched sulfosuccinate ester represented by the following general formula (a1):

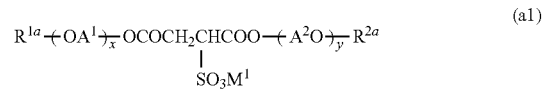

$$R^{1a}\text{−}(OA^1)_x\text{−}OCOCH_2CHCOO\text{−}(A^2O)_y\text{−}R^{2a}$$
$$|$$
$$SO_3M^1$$

wherein $R^{1a}$ and $R^{2a}$ are each independently a branched alkyl group with 9 or 10 carbons; $A^1$ and $A^2$ are each independently an alkylene group with 2 or more and 4 or less carbons, and x and y are average numbers of added moles and each independently 0 or more and 6 or less; and $M^1$ is a hydrogen atom or a cationic ion.

<5>
The surfactant composition according to <4>, wherein the numbers of side chains in $R^{1a}$ and $R^{2a}$ in the general formula (a1) are the same or different.

<6>
The surfactant composition according to <4> or <5>, wherein the numbers of side chains in $R^{1a}$ and $R^{2a}$ in the general formula (a1) are each 1 or more, and preferably 3 or less and more preferably 2 or less.

<7>
The surfactant composition according to any of <4> to <6>, wherein the numbers of branching carbons in $R^{1a}$ and $R^{2a}$ in the general formula (a1) are the same or different.

<8>
The surfactant composition according to any of <4> to <7>, wherein the numbers of branching carbons in $R^{1a}$ and $R^{2a}$ in the general formula (a1) are each 1 or more, and preferably 3 or less and furthermore preferably 2 or less.

<9>
The surfactant composition according to any of <4> to <8>, wherein the branched alkyl groups of $R^{1a}$ and $R^{2a}$ in the general formula (a1) each independently have 9 or 10 carbons in total, each independently have a main chain with 6 or 7 carbons, each independently have a side chain with 1 or more and 3 or less constituting carbons and each independently have one side chain.

<10>
The surfactant composition according to any of <4> to <9>, wherein $R^{1a}$ and $R^{2a}$ in the general formula (a1) are the same or different, and each a branched alkyl group selected from a 2-propylheptyl group and a 3,5,5-trimethylhexyl group.

<11>
The surfactant composition according to any of <4> to <10>, wherein x and y in the general formula (a1) are each independently 0.

<12>
The surfactant composition according to any of <4> to <11>, wherein $M^1$ in the general formula (a1) is an alkali metal ion.

<13>
The surfactant composition according to any of <1> to <12>, wherein component (a) is a branched alkyl sulfosuccinate diester having branched alkyl groups with 9 or 10 carbons.
<14>
The surfactant composition according to any of <1> to <13>, wherein component (a) is an alkali metal salt.
<15>
The surfactant composition according to any of <1> to <14>, wherein the composition contains component (a) in an amount of preferably 0.05 mass % or more, more preferably 0.1 mass % or more and further preferably 0.25 mass % or more, and preferably 20 mass % or less, more preferably 15 mass % or less, further preferably 10 mass % or less and furthermore preferably 5 mass % or less.
<16>
The surfactant composition according to any of <1> to <15>, wherein component (b) is one or more surfactants selected from nonionic surfactants and anionic surfactants other than component (a).
<17>
The surfactant composition according to <16>, wherein the anionic surfactants other than component (a) are compounds of the following general formula (b1):

$R^{1b}—(OA^{1b})_p-OSO_3M$ (b1)

wherein $R^{1b}$ is a hydrocarbon group, preferably an alkyl group, with 10 or more and 16 or less carbons, $A^{1b}$ is an alkylene group with 2 or 3 carbons and preferably an ethylene group, and p is an average number of added moles, and 0 or more and 5 or less, preferably 0 or more and 3 or less and more preferably 0 or more and 2.5 or less; and M is a hydrogen atom or a cationic ion.
<18>
The surfactant composition according to <17>, wherein M in the general formula (b1) is an alkali metal ion.
<19>
The surfactant composition according to any of <16> to <18>, wherein the nonionic surfactants are one or more nonionic surfactants selected from polyoxyalkylene monoalkyl or alkenyl ethers and alkyl (poly)glycosides (glycoside-type nonionic surfactants).
<20>
The surfactant composition according to <19>, wherein the polyoxyalkylene monoalkyl or alkenyl ethers are compounds of the following general formula (b2):

$R^{2b}—O-(A^{2b}O)_n—H$ (b2)

wherein $R^{2b}$ is a hydrocarbon group, preferably an alkyl group, with 10 or more and 18 less and preferably 10 or more and 14 or less carbons, $A^{2b}$ is an alkylene group with 2 or 3 carbons and preferably an ethylene group, and n is an average number of added moles, and a number of 3 or more and 25 or less, preferably 3 or more and 20 or less and more preferably 3 or more and 15 or less.
<21>
The surfactant composition according to <19> or <20>, wherein the alkyl glycosides are compounds of the following general formula. (b3):

$R^{3b}—(OR^{4b})_mG_z$ (b3)

wherein $R^{2b}$ is a linear alkyl group with 8 or more and preferably 10 or more, and 16 or less and preferably 14 or less carbons; $R^{4b}$ is an alkylene group with 2 or more and 4 or less carbons, preferably an ethylene group or a propylene group and more preferably an ethylene group; G is a residue derived from a reducing sugar; m is a number of 0 or more and 6 or less on average; and z is a number of 1 or more, and 10 or less, preferably 5 or less and more preferably 2 or less on average.
<22>
The surfactant composition according to any of <1> to <21>, wherein a mass ratio of the content of component (a) to the content of component (b), component (a)/component (b), is preferably 0.05 or more, more preferably 0.1 or more, further preferably 0.2 or more and furthermore preferably 0.5 or more, and preferably 5 or less, more preferably 1.5 or less, more preferably 1.25 or less and further preferably 1.0 or less.
<23>
The surfactant composition according to any of <1> to <22>, wherein the composition contains component (b) in an amount of preferably 0.1 mass % or more, more preferably 0.15 mass % or more and further preferably 0.25 mass % or more, and preferably 35 mass % or less, more preferably 20 mass % or less, further preferably 10 mass % or less and furthermore preferably 6 mass % or less from the viewpoint of foaming performance.
<24>
The surfactant composition according to any of <1> to <23>, wherein the composition contains (c) a solvent [hereinafter referred to as component (c)].
<25>
The surfactant composition according <24>, wherein component (c) is a water-soluble organic solvent with preferably 2 or more and more preferably 3 or more, and preferably 10 or less and more preferably 8 or less carbons.
<26>
The surfactant composition according to <24> or <25>, wherein component (c) is one or more water-soluble organic solvents selected from (c1) monohydric or polyhydric alcohols and (c2) glycol ethers.
<27>
The surfactant composition according to any <24> to <26>, wherein component (c) is one or more water-soluble organic solvents selected from benzyl alcohol, ethanol, propylene glycol, butyldiglycol and phenoxyethanol.
<28>
The surfactant composition according to any of <24> to <27>, wherein the composition contains butyldiglycol as component (c).
<29>
The surfactant composition according to any <24> to <28>, wherein the composition contains component (c) in an amount of preferably 1 mass % or more, more preferably 2 mass % or more and further preferably 3 mass % or more, and preferably 15 mass % or less, more preferably 12 mass % or less and further preferably 8 mass % or less.
<30>
The surfactant composition according to any of <1> to <29>, wherein the composition contains water and is further a liquid composition containing water.
<31>
A method for producing a surfactant composition including, mixing components (a) and (b).
<32>
The method for producing a surfactant composition according to <31>, wherein component (b) is one or more surfactants selected from nonionic surfactants and anionic surfactants other than component (a), and components (a) and (b) are mixed such that a mass ratio of a mixing amount of component (a) to a mixing amount of component (b), component (a)/component (b), is 0.05 or more, further 0.1 or more, further 0.2 or more and further 0.5 or more, and further 5 or less, further 1.5 or less, further 1.25 or less and further 1.0 or less.

<33>
The method for producing a surfactant composition according to <31> or <32>, wherein the method is a method for producing the surfactant composition according to any of <1> to <30>.

<34>
A foaming control agent composed of (a) a branched alkyl sulfosuccinate ester having a branched alkyl group with 9 or 10 carbons [hereinafter referred to as component (a)] for use in a composition containing (b) a surfactant other than component (a) [hereinafter referred to as component (b)].

<35>
The foaming control agent according to <34>, wherein the agent is used such that a mass ratio of component (a) to component (b), component (a) component (b), is preferably 0.01 or more, more preferably 0.05 or more and further preferably 0.1 or more, and preferably 1.5 or less, more preferably or less and further preferably 0.5 or less.

<36>
A method for controlling foaming performance of a surfactant composition including, adding (a) a branched alkyl sulfosuccinate ester having a branched alkyl group with 9 or 10 carbons [hereinafter referred to as component (a)] to a composition containing (b) a surfactant other than component [hereinafter referred to as component (b)] to control foaming performance of the composition.

<37>
The method for controlling foaming performance of a surfactant composition according to <36>, wherein component (b) is one or more surfactants selected from nonionic surfactants and anionic surfactants other than component (a).

<38>
The method for controlling foaming performance of a surfactant composition according to <36> or <37>, wherein component (a) added such that a mass ratio of the addition amount of component (a) to the content of component (b) in the composition, component (a)/component (b), is 0.05 or more and 5 or less.

<39>
The method for controlling foaming performance of a surfactant composition according to any of <36> to <38>, wherein the control of foaming performance includes at least one of the improvement of foamability and stabilization of foam.

EXAMPLES

The pump foamer container described in FIG. 1 of JP-A 2008-260852 was filled with each of the surfactant compositions in Tables 1 to 3. Here, one mesh with a mesh size of 200 per inch was attached to the foam discharge mechanism. Then, the pump head part at the top of the container was pushed fully three consecutive times, thereby forming 3 g of foam in a 500-ml graduated cylinder. Note that it was pushed fully at a rate of 1 second per push.

Next, 100 mL of ion exchange water was added to the foam for about 5 seconds from a position 30 cm apart in height through a means for introducing ion exchange water (handmade watering can) placed over the graduated cylinder, and the amount of foam 30 seconds after the addition of water was measured as foamability (initial foam amount). In this evaluation, a foamability of 60 mL or more is preferable. With the point of time when ion exchange water was first added as the start of a test, the addition of 100 mL of ion exchange water was thereafter repeated three more times every minute after the start of the test (the total addition amount of ion exchange water was 400 mL). The amount of foam was measured 30 seconds after the addition of a total of 400 mL of ion exchange water was completed, and a numerical value determined by the following formula was used as foam stability. In this evaluation, a foam stability of 60% or more is preferable.

Foam stability (%)=(amount of foam after addition of 400 mL of ion exchange water/initial foam amount)×100

TABLE 1

| | | | | Example | | | | | | | Comparative example | |
|---|---|---|---|---|---|---|---|---|---|---|---|---|
| | | | | 1-1 | 1-2 | 1-3 | 1-4 | 1-5 | 1-6 | 1-7 | 1-1 | 1-2 |
| Surfactant composition | Formulation amount (mass %) | (a) | Sodium bis-(2-propylheplyl) sulfosuccinate | 0.25 | 0.25 | 0.25 | | | | 0.25 | | |
| | | | Sodium bis-(3,5,5-trimethylhexyl) sulfosuccinate | | | | 0.25 | 0.25 | 0.25 | | | |
| | | (a') | Sodium bis-(2-ethylhexyl) sulfosuccinate | | | | | | | 0.25 | 0.25 | 0.25 |
| | | | Sodium bis-(dodecyl) sulfosuccinate | | | | | | | | | |
| | | (b) | Sodium polyoxyethylene (average 2.2 mol) lauryl ether sulfale | 0.25 | | | 0.25 | | | | 0.25 | |
| | | | Alkyl glycoside | | 0.25 | | | 0.25 | | | | 0.25 |
| | | | Polyoxyethylene alkyl ether | | | 0.25 | | | 0.25 | | | |
| | | (c) | Butyldiglycol | 1 | 1 | 1 | 1 | 1 | 1 | 1 | 1 | 1 |
| | | | Water | Balance | Balance | Balance | Balance | Balance | Balance | Balance | Balance | Balance |
| | | | Total | 100 | 100 | 100 | 100 | 100 | 100 | 100 | 100 | 100 |

TABLE 1-continued

|  |  |  |  |  |  |  |  |  |
|---|---|---|---|---|---|---|---|---|
| (a)/(b) (mass ratio) | 1.0 | 1.0 | 1.0 | 1.0 | 1.0 | 1.0 | 1.0*1 | 0 | 0 |
| pH (25° C.) | 6 | 6 | 6 | 6 | 6 | 6 | 6 | 6 | 6 |
| Foamability (mL) | 110 | 75 | 65 | 80 | 75 | 75 | 75 | 85 | 75 |
| Foam stability (%) | 77 | 80 | 77 | 69 | 73 | 67 | 67 | 35 | 53 |

|  |  |  |  | Comparative example |  |  |  |  |  |  |  |  |
|---|---|---|---|---|---|---|---|---|---|---|---|---|
|  |  |  |  | 1-3 | 1-4 | 1-5 | 1-6 | 1-7 | 1-8 | 1-9 | 1-10 | 1-11 |
| Surfactant composition | Formulation amount (mass %) | (a) | Sodium bis-(2-propylheptyl) sulfosuccinate |  |  |  |  |  |  |  | 0.5 |  |
|  |  |  | Sodium bis-(3,5,5-trimethylhexyl) sulfosuccinate |  |  |  |  |  |  |  |  |  |
|  |  | (a') | Sodium bts-(2-ethylhexyl) sulfosuccinate | 0.25 |  |  |  |  |  |  |  | 0.5 |
|  |  |  | Sodium bis-(dodecyl) sulfosuccinate |  | 0.25 | 0.25 | 0.25 |  |  |  |  |  |
|  |  | (b) | Sodium polyoxyethylene (average 2.2 mol) lauryl ether sulfate |  |  | 0.25 |  |  | 0.5 |  |  |  |
|  |  |  | Alkyl glycoside |  |  |  | 0.25 |  |  | 0.5 |  |  |
|  |  |  | Polyoxyethylene alkyl ether | 0.25 |  |  | 0.25 |  |  | 0.5 |  |  |
|  |  | (c) | Butyldiglycol | 1 | 1 | 1 | 1 | 1 | 1 | 1 | 1 | 1 |
|  |  |  | Water | Balance | Balance | Balance | Balance | Balance | Balance | Balance | Balance | Balance |
|  |  |  | Total | 100 | 100 | 100 | 100 | 100 | 100 | 100 | 100 | 100 |
|  | (a)/(b) (mass ratio) |  |  | 0 | 0 | 0 | 0 | 0 | 0 | 0 | — | — |
|  | pH (25° C.) |  |  | 6 | 6 | 6 | 6 | 6 | 6 | 6 | 6 | 6 |
| Foamability (mL) |  |  |  | 80 | 50 | 50 | 70 | 80 | 85 | 60 | 50 | 60 |
| Foam stability (%) |  |  |  | 50 | 80 | 100 | 57 | 56 | 59 | 8 | 10 | 0 |

*1In example 1-7, (a)/(b) was given with component (at) as component (b).

TABLE 2

|  |  |  |  | Example |  |  |  |  |  |  |  | Comparative example |  |
|---|---|---|---|---|---|---|---|---|---|---|---|---|---|
|  |  |  |  | 2-1 | 2-2 | 2-3 | 2-4 | 2-5 | 2-6 | 2-7 | 2-8 | 2-1 | 2-2 |
| Surfactant composition | Formulation amount (mass %) | (a) | Sodium bis-(2-propylheptyl) sulfosuccinate | 0.05 | 0.1 | 0.2 | 0.3 | 0.1 | 0.5 | 0.5 | 0.5 |  |  |
|  |  | (a') | Amine oxide |  |  |  |  |  |  |  |  | 0.1 |  |
|  |  |  | Sulfobetaine |  |  |  |  |  |  |  |  |  | 0.1 |
|  |  | (b) | Sodium polyoxyethylene (average 2.2 mol) lauryl ether sulfate |  |  |  |  |  | 5 |  |  |  |  |
|  |  |  | Alkyl glycoside | 0.45 | 0.4 | 0.3 | 0.2 |  |  | 5 |  | 0.4 | 0.4 |
|  |  |  | Polyoxyethylene alkyl ether |  |  |  |  | 0.4 |  |  | 5 |  |  |
|  |  | (c) | Butyldiglycol | 1 | 1 | 1 | 1 | 1 | 1 | 1 | 1 | 1 | 1 |
|  |  |  | Water | Balance | Balance | Balance | Balance | Balance | Balance | Balance | Balance | Balance | Balance |
|  |  |  | Total | 100 | 100 | 100 | 100 | 100 | 100 | 100 | 100 | 100 | 100 |
|  | (a)/(b) (mass ratio) |  |  | 0.11 | 0.25 | 0.67 | 1.5 | 0.25 | 0.1 | 0.1 | 0.1 | — | — |
|  | pH (25° C.) |  |  | 6 | 6 | 6 | 6 | 6 | 6 | 6 | 6 | 6 | 6 |
| Foamability (mL) |  |  |  | 70 | 60 | 60 | 60 | 70 | 60 | 75 | 70 | 50 | 70 |
| Foam stability (%) |  |  |  | 71 | 92 | 92 | 75 | 71 | 83 | 93 | 100 | 4 | 14 |

TABLE 3

| | | | | Example | | | | | | | | | | |
|---|---|---|---|---|---|---|---|---|---|---|---|---|---|---|
| | | | | 3-1 | 3-2 | 2-1 | 2-2 | 2-3 | 2-4 | 3-3 | 3-4 | 3-5 | 1-1 | 3-6 |
| Surfactant composition | Formulation amount (mass %) | (a) | Sodium bis-(2-propylheptyl) sulfosuccinate | 0.01 | 0.03 | 0.05 | 0.1 | 0.2 | 0.3 | 0.35 | 0.42 | 0.03 | 0.25 | 0.35 |
| | | (a') | Amine oxide Sulfobetaine | | | | | | | | | | | |
| | | (b) | Sodium polyoxyethylene (average 2.2 mol) lauryl ether sulfate | | | | | | | | | 0.47 | 0.25 | 0.15 |
| | | | Alkyl glycoside | 0.49 | 0.47 | 0.45 | 0.4 | 0.3 | 0.2 | 0.15 | 0.08 | | | |
| | | | Polyoxyethylene alkyl ether | | | | | | | | | | | |
| | | (c) | Butyldiglycol | 1 | 1 | 1 | 1 | 1 | 1 | 1 | 1 | 1 | 1 | 1 |
| | | | Water | Balance | Balance | Balance | Balance | Balance | Balance | Balance | Balance | Balance | Balance | Balance |
| | | | Total | 100 | 100 | 100 | 100 | 100 | 100 | 100 | 100 | 100 | 100 | 100 |
| | (a)/(b) (mass ratio) | | | 0.02 | 0.064 | 0.11 | 0.25 | 0.67 | 1.5 | 2.3 | 5.3 | 0.064 | 1.0 | 2.3 |
| | pH (25° C.) | | | 6 | 6 | 6 | 6 | 6 | 6 | 6 | 6 | 6 | 6 | 6 |
| Foamability (mL) | | | | 60 | 60 | 70 | 60 | 60 | 60 | 65 | 60 | 65 | 110 | 61 |
| Foam stability (%) | | | | 60 | 65 | 71 | 92 | 92 | 75 | 65 | 60 | 62 | 77 | 65 |

Some of the components in the tables are listed below. Note that component (a'), which is also component (b), shown as component (a') is the tables for convenience as it was used for a comparison with component (a).

Alkyl glycoside: AG-124, manufactured by Kao Corporation

Polyoxyethylene alkyl ether: a polyoxyethylene alkyl ether, the number carbons in the alkyl group 13, the average number of added moles of ethylene oxide 7, SOFTANOL 70H, manufactured by NIPPON SHOKUBAT CO., LTD.

Amine oxide: AMPHITOL 20N, manufactured by Kao Corporation

Sulfobetaine: AMPHITOL 20HD, manufactured by Mao Corporation

Butyldiglycol: BDG, manufactured by NIPPON NYUKAZAI CO., LTD., ClogPow 0.66

The invention claimed is:

1. A surfactant composition, comprising:
   component (a): an alkali metal salt of a branched alkyl sulfosuccinate ester having a branched alkyl group, wherein the branched alkyl group has a main chain with 6 or 7 carbons and one or more side chains and the side chains have 3 carbons in total; and
   component (b): a surfactant other than the component (a), wherein a mass ratio of the component (a) to the component (b) is 0.05 or more and 5 or less.

2. The surfactant composition according to claim 1, wherein the branched alkyl group of the component (a) is a branched alkyl group selected from the group consisting of a 2-propylheptyl group and a 3,5,5-trimethylhexyl group.

3. The surfactant composition according to claim 1, wherein the component (b) is one or more surfactants selected from the group consisting of a nonionic surfactant and an anionic surfactant.

4. A method for controlling foaming performance of a composition comprising a component (b), the method comprising:
   adding component (a), which is an alkali metal salt of a branched alkyl sulfosuccinate ester having branched alkyl group, wherein the branched alkyl group has a main chain with 6 or 7 carbons and one or more side chains and the side chains have 3 carbons in total, to the composition comprising the component (b), which is a surfactant other than the component (a),
   wherein a mass ratio of the component (a) to the component (b) is 0.05 or more and 5 or less.

5. The method according to claim 4, wherein the component (b) is one or more surfactants selected from the group consisting of a nonionic surfactant and an anionic surfactant.

6. The method according to claim 4, wherein the addition of the component (a) improves foamability and/or stabilizes foam.

7. The surfactant composition according to claim 1, further comprising:
   component (c): one or more water-soluble organic solvents selected from the group consisting of benzyl alcohol, ethanol, propylene glycol, butyldiglycol, and phenoxyethanol.

8. The surfactant composition according to claim 1, wherein the component (a) is a foaming control agent.

9. The method according to claim 4, wherein the composition further comprises:
   component c), which is one or more water-soluble organic solvents selected from the group consisting of benzyl alcohol, ethanol, propylene glycol, butyldiglycol, and phenoxyethanol.

10. The method according to claim 4, further comprising:
    discharging the composition in foam form from a container having a foam discharge mechanism.

* * * * *